(12) United States Patent
Abe

(10) Patent No.: US 9,724,236 B2
(45) Date of Patent: Aug. 8, 2017

(54) OPHTHALMIC LASER TREATMENT APPARATUS

(75) Inventor: Hitoshi Abe, Okazaki (JP)

(73) Assignee: NIDEK CO., LTD., Gamagori-shi (JP)

( * ) Notice: Subject to any disclaimer, the term of this patent is extended or adjusted under 35 U.S.C. 154(b) by 231 days.

(21) Appl. No.: 13/073,256

(22) Filed: Mar. 28, 2011

(65) Prior Publication Data
US 2011/0245816 A1 Oct. 6, 2011

(30) Foreign Application Priority Data

Mar. 31, 2010 (JP) ................. 2010-084700
Jan. 27, 2011 (JP) ................. 2011-015802

(51) Int. Cl.
*A61F 9/008* (2006.01)

(52) U.S. Cl.
CPC ...... *A61F 9/00821* (2013.01); *A61F 2009/00863* (2013.01); *A61F 2009/00897* (2013.01)

(58) Field of Classification Search
CPC ............ A61F 2009/00897; A61F 9/008; A61F 2009/00863; A61F 9/00821; A61B 2018/2025; A61B 2018/2085; A61B 2018/2272
See application file for complete search history.

(56) References Cited

U.S. PATENT DOCUMENTS

| | | | |
|---|---|---|---|
| 5,906,609 A * | 5/1999 | Assa et al. | 606/9 |
| 5,938,657 A * | 8/1999 | Assa et al. | 606/9 |
| 6,585,725 B1 * | 7/2003 | Mukai | 606/10 |
| 6,673,061 B2 | 1/2004 | Abe | |
| 7,173,745 B2 | 2/2007 | Dair et al. | |
| 2002/0099363 A1 | 7/2002 | Woodward et al. | |

(Continued)

FOREIGN PATENT DOCUMENTS

| | | |
|---|---|---|
| CN | 101553280 A | 10/2009 |
| EP | 1 210 915 A2 | 6/2002 |

(Continued)

OTHER PUBLICATIONS

U.S. Appl. No. 13/073,278, filed Mar. 28, 2011 in the name of Yokosuka.

(Continued)

*Primary Examiner* — Gary Jackson
*Assistant Examiner* — Scott T Luan
(74) *Attorney, Agent, or Firm* — Oliff PLC

(57) ABSTRACT

An ophthalmic laser treatment apparatus, comprising: an emitted treatment laser beam; an emitted aiming beam; an irradiation unit including a zoom lens and a scanner for scanning in two dimensions, and being arranged to irradiate both beams to the eye; an irradiation pattern setting unit including a switch for setting an irradiation pattern in which a plurality of spots is arranged; and a controller for controlling the aiming beam based on the set pattern during aiming before irradiation of the treatment beam, the controller being configured to divide the spots in the set pattern into two or more groups and switch the positions of the spots of the aiming beam at a predetermined time interval in each group to irradiate the aiming beam so that the irradiation spots of the aiming beam in a group before switching and another group after switching are not recognized simultaneously by an operator.

15 Claims, 7 Drawing Sheets

(56) References Cited

U.S. PATENT DOCUMENTS

| | | |
|---|---|---|
| 2004/0073200 A1 | 4/2004 | Caudle et al. |
| 2007/0121069 A1* | 5/2007 | Andersen et al. ............ 351/221 |
| 2007/0129775 A1* | 6/2007 | Mordaunt et al. .............. 607/88 |
| 2007/0189664 A1 | 8/2007 | Andersen et al. |
| 2008/0015553 A1 | 1/2008 | Zacharias |
| 2008/0049188 A1* | 2/2008 | Wiltberger ........... A61B 3/0091 351/211 |
| 2009/0093798 A1 | 4/2009 | Charles |
| 2011/0178512 A1* | 7/2011 | Blumenkranz et al. .......... 606/6 |
| 2011/0202046 A1 | 8/2011 | Angeley et al. |
| 2011/0319874 A1* | 12/2011 | Mintz ................ A61F 9/00802 606/4 |

FOREIGN PATENT DOCUMENTS

| | | |
|---|---|---|
| JP | A-02-161930 | 6/1990 |
| JP | A-2001-149403 | 6/2001 |
| JP | A-2002-224154 | 8/2002 |
| JP | A-2006-524515 | 11/2006 |
| JP | A-2009-514564 | 4/2009 |
| WO | WO 2005/065116 A2 | 7/2005 |
| WO | WO 2007/035855 A2 | 3/2007 |
| WO | WO 2007/082102 A2 | 7/2007 |
| WO | WO 2008/112292 A1 | 9/2008 |

OTHER PUBLICATIONS

U.S. Appl. No. 13/073,217, filed Mar. 28, 2011 in the name of Abe.
European Search Report issued in European Patent Application No. 11160416.1; mailed Jul. 13, 2011.
Dec. 13, 2012 Office Action issued in U.S. Appl. No. 13/073,278.
Jun. 25, 2014 Office Action issued in U.S. Appl. No. 13/073,217.
Dec. 4, 2013 Office Action issued in U.S. Appl. No. 13/073,217.
Aug. 19, 2013 Office Action issued in U.S. Appl. No. 13/073,278.
European Search Report issued in European Patent Application No. 11160163.9 mailed Aug. 8, 2011.

* cited by examiner

FIG.4
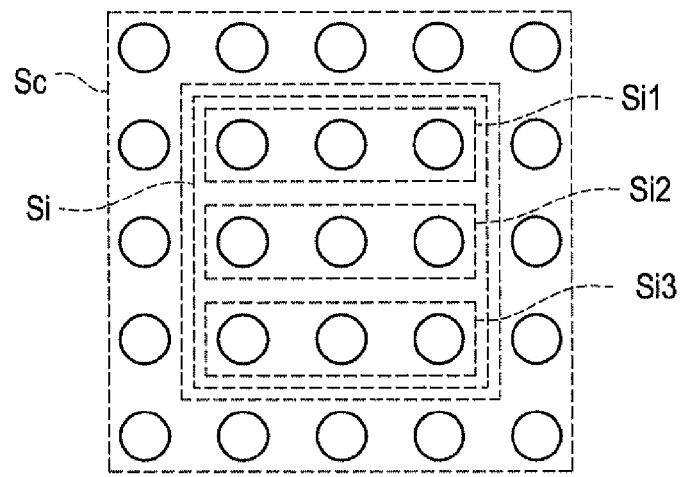
FIG. 5A
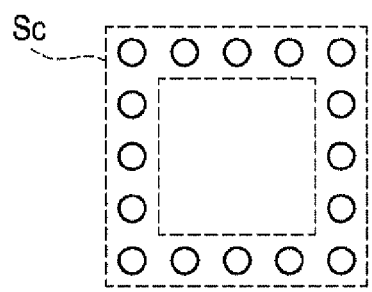
FIG. 5B   FIG. 5C   FIG. 5D
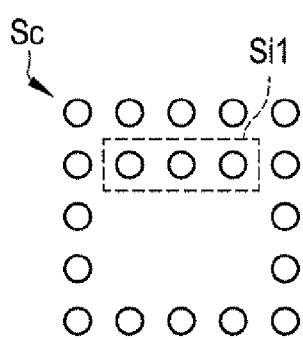 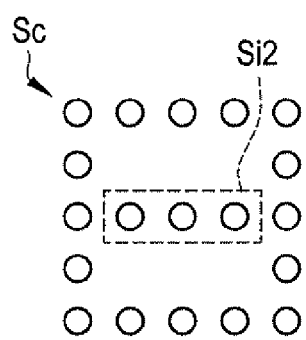 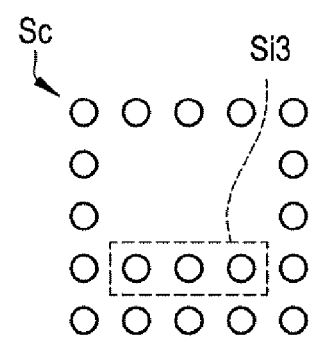

OPHTHALMIC LASER TREATMENT APPARATUS

CROSS-REFERENCE TO RELATED APPLICATIONS

This application is based upon and claims the benefit of priority from the prior Japanese Patent Applications No. 2010-84700 filed Mar. 31, 2010 and No. 2011-15802 filed Jan. 27, 2011, the entire contents of which are incorporated herein by reference.

TECHNICAL FIELD

The present invention relates to an ophthalmic laser treatment apparatus for treating a patient's eye by irradiating a laser beam thereto.

BACKGROUND ART

As one of ophthalmic laser treatment apparatuses, a photocoagulation apparatus is known. For photocoagulation treatment (e.g., panretinal photocoagulation treatment), a treatment laser beam is sequentially irradiated on a spot-by-spot basis to fundus tissues of a patient's eye to thermally photocoagulate the tissues. For irradiation of the treatment laser beam, a visible aiming beam is first irradiated for aiming of the treatment laser beam (for example, see JP 2002-224154A). In recent years, an apparatus has been proposed in which a scanning unit including a galvano mirror and others is installed in a laser-beam delivery unit to scan a treatment laser beam in the form of a spot onto fundus tissues based on a plurality of scanning patterns of spot positions set in advance (for example, see JP 2006-524515A and JP 2009-514564A). This apparatus stores in advance a plurality of predetermined irradiation patterns in a memory, for example, a pattern of spots arranged in a square matrix of 3×3, 5×5, or others, a pattern of spots arranged in a circular form (including a fan-like form), and others so that a desired irradiation pattern is selectable by an operator according to the condition of the tissues. Further, the aiming beam is also irradiated based on the irradiation patterns.

SUMMARY OF INVENTION

Technical Problem

JP 2006-524515A discloses a technique for aiming using an aiming beam, achieved by scanning the aiming beam (irradiating the aiming beam to tissues) at high speeds so that all spots of the aiming beam are simultaneously viewed on spot positions to which a treatment laser beam is to be irradiated. However, when all spots of the aiming beam are visible at the same time, operator's visual field is obstructed by the aiming beam and thus the condition of the aimed fundus tissues is hard to observe. In particular, a larger spot size of the aiming beam has more harmful effects. In the case where an irradiation pattern for irradiating sports in a wide region is set, it is necessary to largely move or displace an irradiation region of the aiming beam in order to check tissues in spot positions. This work is troublesome. Re-aiming also takes much time and labor. A work of switching between irradiation and stop of the aiming beam by a switch operation is also troublesome.

The present invention has been made to solve the above problems and has a purpose to provide an ophthalmic laser treatment apparatus enabling easy check of tissues in aiming positions during aiming using aiming beam spots.

Solution to Problem

To achieve the above purpose, one aspect of the invention provides an ophthalmic laser treatment apparatus for treating a patient's eye, comprising: a treatment laser source for emitting a treatment laser beam; an aiming light source for emitting an aiming beam; an irradiation unit including a zoom lens for changing a size of each irradiation spot of the treatment beam and the aiming beam and a scanner for scanning each irradiation spot on a tissue of the patient's eye in two dimensions, the irradiation unit being arranged to irradiate the treatment beam and the aiming beam to the eye; an irradiation pattern setting unit including a switch for inputting a signal to set an irradiation pattern in which a plurality of irradiation spots of the treatment beam is arranged; and a controller for controlling driving of the irradiation unit to control a position of the irradiation spot of the aiming beam based on the set irradiation pattern during aiming before irradiation of the treatment beam, the controller being configured to divide the irradiation spots of the treatment beam in the set irradiation pattern into two or more groups and switch the positions of the irradiation spots of the aiming beam at a predetermined time interval based on the irradiation spots of the treatment beam in each group to irradiate the aiming beam so that the irradiation spots of the aiming beam in a group before switching and the irradiation spots of the aiming beam in another group after switching are not recognized simultaneously by an operator.

Advantageous Effects of Invention

According to the present invention, it is easy to check the condition of tissues in aiming positions even during aiming using aiming beam spots.

BRIEF DESCRIPTION OF DRAWINGS

FIG. 4 is a view of a square pattern of 5×5 spots;

FIGS. 5A-5D are explanatory views showing irradiation spots of an aiming beam;

DESCRIPTION OF EMBODIMENTS

Figure 1:
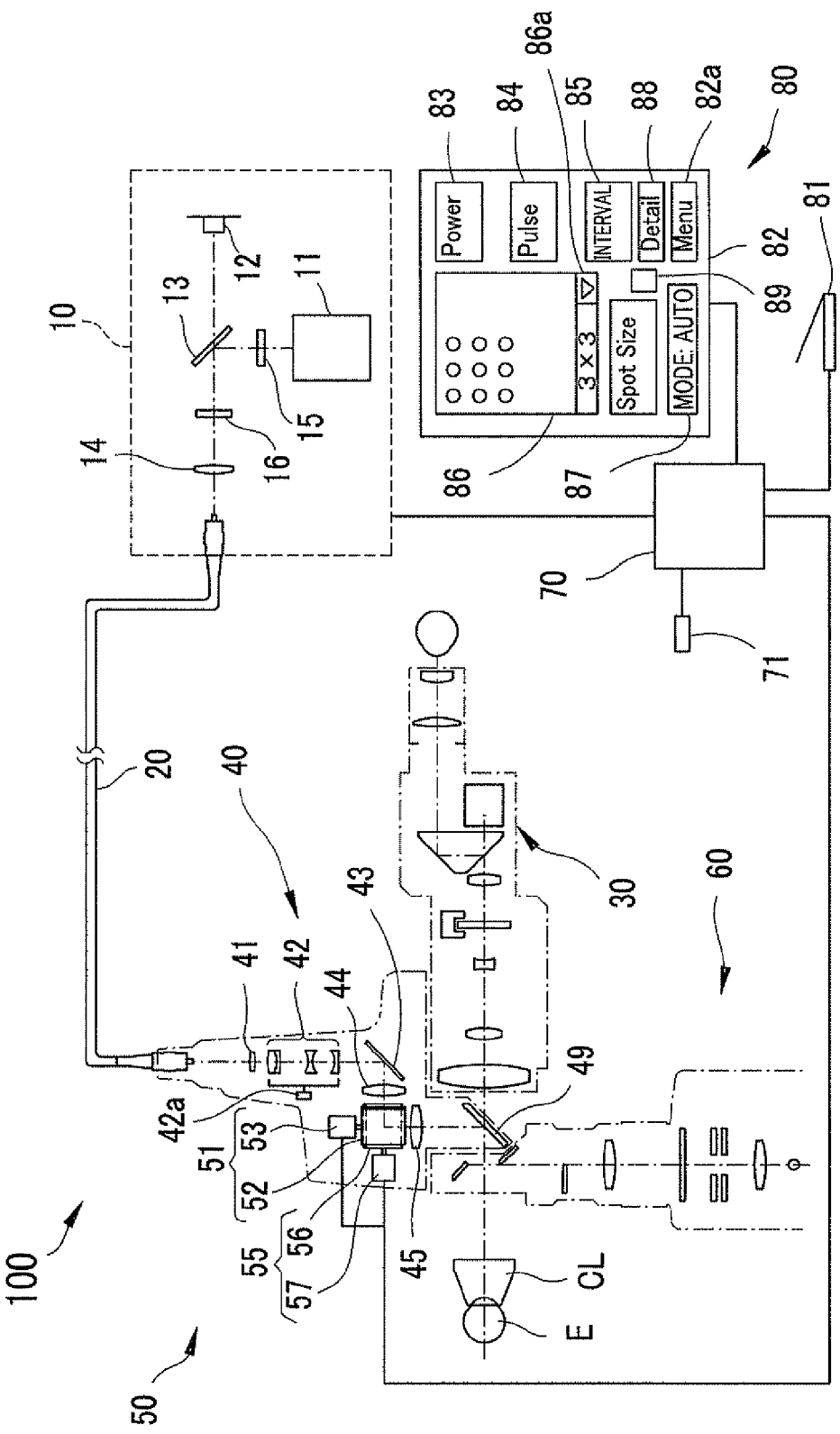
FIG. 1 is a schematic configuration view of optical systems and a control system of an ophthalmic laser treatment apparatus.

A detailed description of a preferred embodiment of the present invention will now be given referring to the accompanying drawings. FIG. 1 is a schematic configuration view showing optical systems and a control system of an ophthalmic laser treatment apparatus for performing photocoagulation treatment and others.

An ophthalmic laser treatment apparatus 100 roughly includes a laser source unit 10, a laser irradiation optical system (an irradiation unit) 40, an observation optical system 30, an illumination optical system 60, a controller 70, and an operation unit 80. The laser source unit 10 includes a treatment laser source 11 for emitting a treatment laser beam, an aiming light source 12 for emitting a visible aiming laser beam (an aiming beam), a beam splitter (a combiner) 13 for combining the treatment laser beam and the aiming beam, and a focusing lens 14. The beam splitter 13 reflects most of the treatment laser beam and transmits a part of the aiming beam. The combined laser beam is focused by the focusing lens 14 to enter an incident end face of an optical fiber 20 for delivering the laser beam to the laser irradiation optical system 40. A first shutter 15 is placed between the laser source 11 and the beam splitter 13 to block the treatment laser beam. Further, a second shutter 16 is placed on an optical path of the aiming beam from the aiming light source 12 and the treatment laser beam from the treatment laser source 11. The second shutter 16 is a safety shutter that is closed in case an abnormality occurs, but also may be used for enabling or blocking irradiation of the aiming beam during scanning of the aiming beam. The first shutter 15 also may be used for enabling or blocking of irradiation of the treatment laser beam. Each shutter may be replaced with a galvano mirror having a function of switching optical paths.

The laser irradiation optical system 40 is configured as a delivery unit mounted in a slit lamp (not shown) in the present embodiment. A laser beam (the treatment laser beam and the aiming beam) emitted from the optical fiber 20 passes through a relay lens 41, zoom lenses 42 movable in an optical axis direction to change a spot size of the laser beam, a mirror 43, and a collimator lens 44. The laser beam then passes through a scanner 50, an objective lens 45, and a reflection mirror 49 and is irradiated onto a fundus of a patient's eye E. The scanner 50 consists of a scanning optical system including a scanner mirror for moving an irradiation direction (an irradiation position) of the laser beam in two dimensions. The scanner 50 includes a first galvano mirror (a galvano scanner) 51 and a second galvano mirror 55. The first galvano mirror 51 includes a first mirror 52 for reflecting the laser beam and an actuator 53 serving as a drive part for driving (rotating) the mirror 52. Similarly, the second galvano mirror 55 includes a second mirror 56 and an actuator 57. The laser beam having passed through each optical element of the laser irradiation optical system 40 is reflected by the reflection mirror 49 and irradiated onto the fundus which is a target plane (onto the tissues) of the eye E through a contact lens CL.

The zoom lenses 42 are held in a lens cam not shown. The lens cam is rotated by operation of an operator to move each zoom lens 42 in an optical axis direction. The positions of the zoom lenses 42 are detected by an encoder 42a attached to the lens cam. The controller 70 receives positional information (a detection signal) of each lens from the encoder 42a and obtains a spot size of the laser beam. The scanner 50 is controlled based on a command signal from the controller 70 to form the laser beam (the spot) in a two-dimensional irradiation pattern on the target plane. The irradiation pattern is an arrangement pattern of spots on the target plane and represents a pattern along which spots are to be scanned on the target plane. The reflection mirror 49 is connected to a mechanism (a hand-operated manipulator), not shown, which is operated by the operator, to tilt the optical axis of the laser beam in two dimensions.

Figure 2:
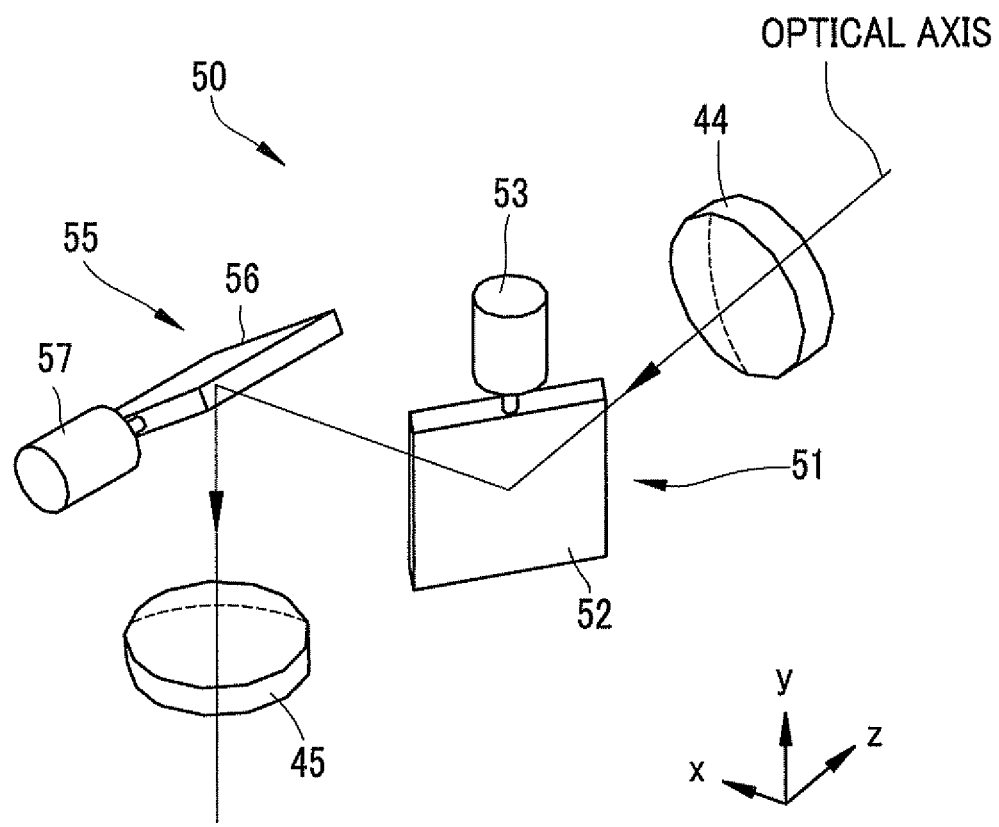
FIG. 2 is a perspective view of a scanner.

The structure of the scanner 50 will be explained. FIG. 2 is a perspective view of the scanner 50. The mirror 52 is attached to the actuator 53 to swing a reflection plane in an x-direction. On the other hand, the mirror 56 is attached to the actuator 57 to swing a reflection plane in a y-direction. In the present embodiment, the rotation axis of the mirror 52 coincides with a y-axis and the rotation axis of the mirror 56 coincides with a z-axis. Further, the actuators 53 and 57 are connected to and separately driven by the controller 70. Each of the actuators 53 and 57 contains a motor and a potentiometer (both not shown). The mirrors 52 and 56 are independently rotated (swung) based on command signals from the controller 70. At that time, positional information representing how much the mirrors 52 and 56 have been rotated is transmitted from the potentiometers of the actuators 53 and 57 to the controller 70. Accordingly, the controller 70 ascertains the rotational positions of the mirrors 52 and 56 with respect to the command signals.

The observation optical system 30 and the illumination optical system 60 are installed in the slit lamp. The observation optical system 30 includes an objective lens and further a variable magnification optical system, a protection filter, erect prisms, a field diaphragm, eyepieces, and others. The illumination optical system 60 for illuminating the eye E with slit light includes an illumination light source, a condenser lens, a slit, a projection lens, and others.

To the controller 70, there are connected a memory 71, the light sources 11 and 12, the encoder 42a, the actuators 53 and 57, the operation unit 80, and a footswitch 81 serving as a device for inputting a trigger for irradiation of the laser beam. The operation unit 80 includes a touch panel display 82 used for setting laser irradiation conditions, and changing and inputting the irradiation patterns. The display 82 is provided with various panel switches for setting parameters of the laser irradiation conditions. The display 82 has a graphical user interface function enabling a user to visually check and set numerical values and others. For items of the irradiation conditions, there are prepared a setting part 83 for output power of the treatment laser beam, a setting part 84 for an irradiation time (a pulse width), a setting part 85 for a halt time (a time interval of irradiation of the treatment laser beam), a setting part 86 for irradiation patterns of the treatment laser beam (arrangement patterns of spot positions of the treatment laser beam to be formed on the target plane), a mode setting part 87 (a mode selector) for setting an aiming mode, a details setting switch 88, a menu switch 82a for calling up other setting parts and others, etc. With the mode setting part 87, a plurality of aiming modes is selectively set.

At the touch of each item on the display 82, numeral values can be set. For instance, when an operator touches the switch 86a, selectable options are displayed in a pull-down menu. When the operator chooses a numeral value from the options, a set value in that item is determined. A plurality of irradiation patterns is previously prepared to be selectable by the operator on the display 82. As the irradiation patterns prepared by an apparatus manufacturer, for example, there are a pattern of spots (spot positions) arranged in a square matrix of 2×2 (height×width), 3×3, 4×4 or others (a square pattern), a pattern of spots arranged in a curve form (or a circular arc form) (a curve pattern or a circular arc pattern), a pattern of spots arranged in an outer circumferential direction and an inner circumferential direction to form a fan-like form (a fan-like pattern), a pattern of spots arranged in a circular form (a circular pattern), a segmental pattern of the circular pattern (a circular segmental pattern), a linear pattern of spots arranged in a linear form, and other patterns. They are stored in the memory 71. The circular pattern is prepared in the form of a half circle, a three-quarter circle, a one-quarter circle, etc.

Herein, one or some of the aforementioned irradiation patterns are each defined as one pattern including small patterns (representing small groups together constituting the irradiation pattern) arranged in several lines in each of which spots are arranged in a line (a linear or curved line). For instance, a 3×3 square pattern is configured as one pattern including small patterns arranged in three lines in each of which three spots are arranged in a line (a horizontally extending line). Further, the fun-like pattern is configured as one pattern (herein, referred to as a triple arc) including small patterns arranged in three lines in each of which three spots are arranged in a curve.

The irradiation pattern is selectable from the plurality of irradiation patterns stored in the memory 71 by use of the switch 86a of the setting part 86. A selected irradiation pattern is displayed on a screen of the setting part 86. Further, the information of the spot size of the laser beam changed by movement of the zoom lenses 42 is displayed on the display 82.

Herein, the radius (or the diameter) of the circular pattern is set by the operation unit 80. Spots are arranged on a circle with the set radius or diameter (i.e., in a curve forming the circle). At that time, the number of spots of the circular pattern depends on settings of the spot size and the spot interval (pitch). In this embodiment, the number of spots is selectable in a range from 3 to 32.

When the footswitch 81 is pressed down by the operator, the controller 70 irradiates the laser beam based on the settings of various parameters to form a pattern of the treatment laser beam on the target plane. Specifically, the controller 70 controls the light source 11 and controls the scanner 50 based on the set pattern to form the pattern of the treatment laser beam on the target plane (the fundus).

Figure 3:
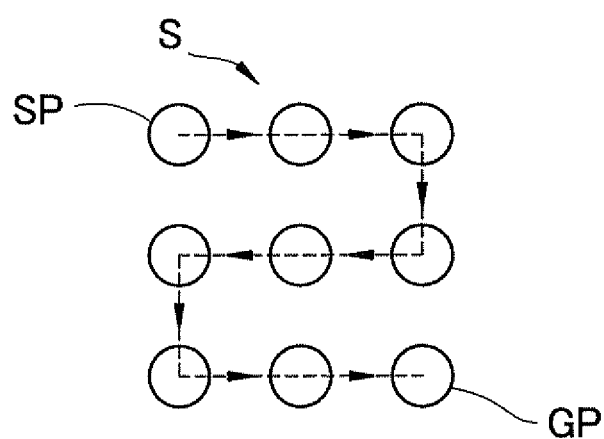
FIG. 3 is a view showing one example of irradiation patterns of spots of a treatment laser beam.

FIG. 3 shows one example of the irradiation patterns of the treatment laser beam spots. As shown in the figure, this pattern is configured by arranging spots S in a 3×3 square matrix. Herein, the spots S represent both the aiming beam and the treatment laser beam. Based on such pattern, the treatment laser beam and the aiming beam are scanned by the scanner 50 to form the pattern on the target plane. During irradiation of the treatment laser beam, the spot S starts to be irradiated from a start position SP and is scanned toward an end position GP in two dimensions. In the present embodiment, as indicated by arrows in the figure, the laser beam is scanned to sequentially move from one to adjacent spots S so as to enable movement between spots S as efficient as possible.

The interval (pitch) between the spots S can be arbitrarily set in a range from 0.5 to 2 times the spot diameter by use of the spot interval setting part 89 on the display 82. In the case of the square pattern shown in FIG. 3, the spots S are arranged at equal intervals in vertical and horizontal directions. Further, in the circular pattern, the spots are arranged in a circle (the controller 70 scans the treatment laser beam and the aiming beam) based on the diameter (or the radius) of the circle, the spot size, and the spot interval which are set in advance.

The apparatus having the aforementioned configuration will be explained with a focus on an aiming operation by irradiation of the aiming beam. Prior to a surgical operation, conditions for the operation such as irradiation pattern, spot size of the treatment laser beam, power of the treatment laser beam, and irradiation time of the laser beam at each spot are set. For instance, for panretinal photocoagulation treatment, it is assumed that a spot size of the treatment laser beam is set to 200 μm and a 5×5 square pattern is selected as the irradiation pattern in advance, respectively. As an aiming beam mode, a first aiming mode and a second aiming mode are selectable by the mode setting part 87. The case where the first aiming mode is selected is first explained below.

The first aiming mode is a mode in which all aiming beam spots are simultaneously recognized or seen as is conventionally done. An operator observes, through the observation optical system 30, the fundus illuminated by illumination light from the illumination optical system 60 and also the spot positions of the irradiated aiming beam, and moves the slit lamp (including the observation optical system 30 and the illumination optical system 60) containing the laser irradiation optical system 40 with respect to the eye E to aim the beam to a treatment area. In the first aiming mode, during aiming, the aiming light source 12 and the scanner 50 are controlled to operate based on the irradiation pattern so that all spots of the irradiation pattern are simultaneously observed by the operator by visual persistence of the aiming beam. Specifically, at each spot position, the driving of the galvano mirrors 51 and 55 of the scanner 50 is stopped and the aiming beam is irradiated with a pulse width (e.g., 10 ms) of a constant time. During movement of the spot to a next position, the aiming beam is not irradiated. If the speed (cycle) of one scan to each spot position is higher than the visual persistence time of a human eye, all the spots are simultaneously observed by the operator.

A case where the second aiming mode is selected is explained below. In the first aiming mode, there is a case where the state of fundus tissues and others in each spot position is hard to check. Particularly, when the irradiation pattern for irradiating a laser beam in a wide range, such as a square pattern of 5×5 spots, is selected, the state of fundus tissues and others is hard to check. In this case, the second aiming mode explained below is appropriately used.

A first example of the second aiming mode is explained. A plurality of spot positions constituting the irradiation pattern is divided into a first region placed on outer circumference to make the operator recognize an irradiation range of the treatment laser beam and a second region inside the first region. A manner of dividing into the first region and the second region is determined by the controller 70 based on the arrangement of spots in the selected irradiation pattern. For instance, the square pattern consisting of the spots arranged in 5×5 is divided into a first region Sc of sixteen spots including at least spots at four corners and a second region Si of nine spots placed inside the first region Sc, as shown in FIG. 4. In at least the second region Si, with respect to the first region, irradiation of the aiming beam and driving of the scanner 50 are controlled intermittently at time intervals so that the operator easily check the condition of an area or portion in each spot position. In other words, in the second region Si, irradiation and stop of the aiming beam is controlled so that the state of the tissues in the spot positions and the aiming beam spots are recognized alternately at a certain time interval (a predetermined time for which the aiming beam spots are not observed simultaneously by the operator).

For the first region Sc, preferably, the irradiation of the aiming beam is controlled so that the spots are simultaneously recognized by the operator. For the second region Si, the spots are further divided into a plurality of sub-regions and the irradiation of the aiming beam is controlled so that the spots are recognized by sub-region by the operator. Herein, the first region Sc and one of the sub-region of the second region Si constitute one group (divide the irradiation pattern). In the 5×5 irradiation pattern in FIG. 4, the second region Si is divided into sub-regions Si1, Si2, and Si3 each including spots arranged in a lateral line.

Concrete control is explained below. From first to fourth scanning, as shown in FIG. 5A, the driving of the scanner 50 and the aiming light source (or the second shutter 16) are controlled by the controller 70 to irradiate the aiming spots only to sixteen spot positions in the first region Sc. At each spot position, the aiming beam is irradiated with a pulse width Ta (e.g., 3 ms) for a constant time. During spot movement, irradiation of the aiming is stopped. In sync with emission of the aiming beam, the galvano mirrors 51 and 55 are stopped to introduce the aiming beam to the spot positions of each group.

In fifth scanning, the driving of the scanner 50 and the aiming source (or the second shutter 16) are controlled to irradiate the aiming spots at spot positions in the sub-region Si1 of the second region Si in addition to the first region Sc as shown in FIG. 5B. From sixth to ninth scanning, the aiming spots are irradiated again only at sixteen spot positions in the first region Sc as shown in FIG. 5A. In following tenth scanning, the aiming spots are irradiated at spot positions in the sub-region Si2 of the second region Si in addition to the first region Sc as shown in FIG. 5C. From eleventh to fourteen scanning, the aiming spots are irradiated again only at sixteen spot positions in the first region Sc as shown in FIG. 5A. In fifteenth scanning, the aiming spots are irradiated at spot positions in the sub-region Si3 of the second region Si in addition to the first region Sc as shown in FIG. 5D. The above cycle from first to fifteenth scanning is subsequently repeated.

In the above example, assuming that the irradiation time (pulse width) of the aiming beam to be irradiated at each spot position is set to 3 ms and the time needed for one spot movement is 1 ms on average, the time for one scanning only in the first region Sc in FIG. 5A is 64 ms (0.064 seconds). If one scanning of the aiming beam irradiation is less than 0.1 seconds, all the spots are likely to be recognized at the same time due to visual persistence by a human eye. The scanning of the spots shown in FIG. 5A is repeated four times and thus this time is 224 ms (0.224 seconds). On the other hand, when the aiming beam is irradiated in the sub-regions Si1, Si2, and Si3 every four scanning operations as in the above example, the time for one scanning is 76 ms (0.076 seconds). Accordingly, the states of the aiming beam in FIGS. 5B, 5C, and 5D are observed every about 0.3 seconds. In other words, the sub-regions Si1, Si2, and Si3 of the second region Si are switched in turn at time intervals of 0.3 seconds so that the spots of one of the sub-regions Si1-Si3 are observed and the spots of other two sub-regions are not observed. During this period, the operator checks the state of the fundus tissues. By the aiming spots in the regions Si1, Si2, and Si3 intermittently observed every about 0.3 seconds, it is possible to ascertain the positional relationship of the spot positions of the treatment laser beam to the treatment area.

After completion of aiming, the irradiation of the treatment laser beam is started upon press of the footswitch 81 by the operator. Upon receipt of a trigger signal from the footswitch 81, the controller 70 controls the laser source 12 to stop emission of the aiming beam and causes the treatment laser source 11 to emit the treatment laser beam and also controls the scanner 50 to sequentially irradiate the treatment laser beam at each spot position (in the 5×5 square pattern). The treatment laser beam is irradiated at each spot position based on a set time of the pulse width of the treatment laser beam. The spot is moved during a halt time of the treatment laser beam.

Since the irradiation of the aiming beam is controlled as above, it is easy to check the state of the fundus tissues and others at each spot position in parallel with aiming to a target treatment area. Specifically, the aiming to the target treatment area can be performed by the aiming beam in the first region Sc representing the irradiation range of the treatment laser beam. Even when the spots in the irradiation pattern are moved to another area as in the panretinal photocoagulation treatment, the aiming can be performed as in the first aiming mode. In the second region Si, on the other hand, the aiming beam is irradiated intermittently, so that the state of the fundus tissues at each spot position can be checked while the aiming beam is not irradiated. Since the aiming beam spots are irradiated at certain time intervals, the spot positions to be irradiated by the treatment laser beam can also be recognized.

In the above example, in the spot positions in the first region Sc, the aiming spots are observed at almost the same time. However, when the state of fundus tissues in those spot positions is to be checked, the irradiation region of the aiming beam is simply displaced by one spot. This is not a large burden and has little trouble to perform aiming again.

The above embodiment may be variously modified. The order of scanning the aiming beam to the sub-regions Si1, Si2, and Si3 of the second region Si (at intervals of four scanning operations) is a mere example. This scanning order is appropriately determined based on a relationship between the number of all spots in the irradiation pattern, the irradiation time of the aiming beam in one spot, and the time needed for one scanning operation.

As an alternative, it may be arranged to irradiate the aiming beam at all spot positions in the second region S2 at intervals of the predetermined number of scanning operations (time) without providing the sub-regions Si1, Si2, and Si3. For instance, the aiming beam is irradiated to the second region Si at intermittent (switching) intervals of 0.1 seconds or more and 3 seconds or less. If the intermittent interval of the aiming beam to the second region Si is less than 0.1 seconds, the spots are simultaneously recognized by visual persistence or as if the spot is flickering. This is not preferable for intermittent observation. If the intermittent interval (switching time) is 3 seconds or more, it is difficult to check the spot positions by use of the aiming beam. Although the intermittent interval of the aiming beam is set to 0.1 seconds or more in the above explanation, a lower limit of the time for one scanning has only to be set to allow the operator to intermittently recognize the aiming beam. For example, one scanning may be set to 0.3 seconds.

Figure 6A:
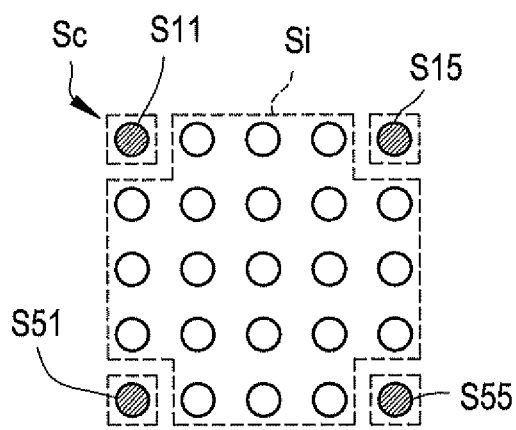
FIG. 6A-6C are explanatory views showing modified examples of the irradiation spots of the aiming beam.
Figure 6B:
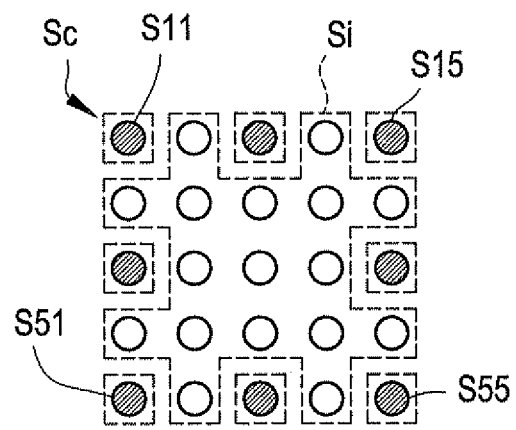

In the example shown in FIG. 4, all the spot positions arranged in the outer circumference are defined as the first region Sc. In the case of the square irradiation pattern, the first region Sc may be defined by a portion including at least spot positions at four corners as shown by oblique lines in FIGS. 6A and 6B. FIG. 6A shows an example that a first region Sc consists of four-corner spot positions S11, S15, S51, and S55. FIG. 6B shows an example that a first region Sc consists of spot positions including four-corner spot positions and spot positions located every two spot positions in the outer circumference.

Figure 6C:
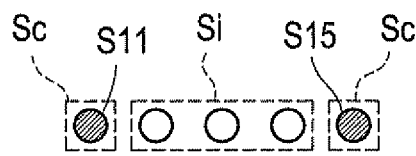

In the case of the linear irradiation pattern in which the spot positions are arranged in a line as shown in FIG. 6C, a first region Sc consists of spot positions S11 and S15 at both ends and a second region Si consists of spot positions between them. In another case where the spot positions are arranged in a circular or fan-like form, as with the manner in FIG. 6B, a first region Sc consists of spot positions skipping one or two spot positions in an outer circumference. In those cases, a second region Si consists of spot positions inside the first region Sc.

As another alternative, in relation to the above examples, the irradiation of the aiming beam may be controlled so that the aiming spots in the first region Sc and the second region Si are separately and intermittently recognized by the operator. For instance, in first to fourth scanning, the aiming beam is irradiated only at the spot positions in the first region Sc. In following fifth to eighth scanning, the aiming beam is irradiated only at the spot positions in the second region Si. This cycle is repeated. In this case, if the time for one scanning is 0.1 second on average, the spot positions in the first region Sc and the second region Si are alternately switched every 0.4 seconds and observed. In this example, the aiming to the target treatment area is enabled while the aiming beam is observed in the first region Sc or the second region Si, and the state of the tissues of the treatment area can be observed while the aiming beam is not observed in each region. In this case, the intermittent interval is preferably set to 0.1 seconds or more and 1 seconds or less as in the above cases.

The scanner 50 may include a member for e.g. tilting a single mirror in x- and y-directions. As an alternative, scanning of the laser beam and others may be conducted by tilting the lens.

As above, the spots in the irradiation pattern set on the display 82 are divided into a plurality of groups and each group is sequentially switched at intervals for which the aiming spots are not simultaneously observed by the operator. Accordingly, the operator can easily observe the fundus tissues at the spot positions not irradiated with the aiming beam.

Figure 7A:
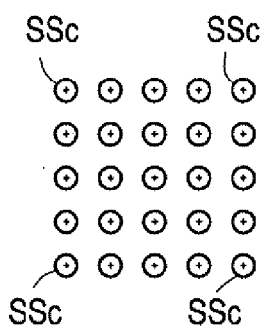
FIGS. 7A-7C are explanatory views showing aiming beam irradiation in a 5×5 irradiation pattern.
Figure 7B:
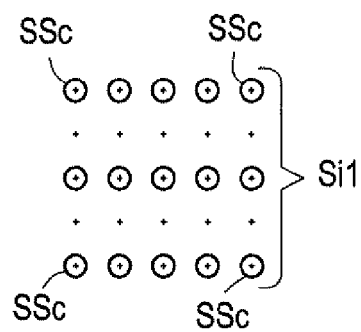
Figure 7C:
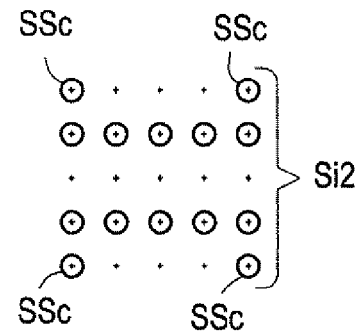

Another modified example of the second aiming mode is explained below. An example that an irradiation pattern consisting of irradiation spots of the treatment beam arranged in three or more lateral lines is first explained. FIG. 7A shows an example of a square pattern consisting of spots arranged in a 5×5 matrix. In this example, the spots are divided into two groups as shown in FIGS. 7B and 7C so that each group includes spots arranged in a line and the spots arranged in the same line are not redundantly included in different group. To be concrete, the first group Si1 consists of the spots arranged in an uppermost line, in a lowermost line, and in a middle, third line as shown in FIG. 7B. The second group Si2 consists of the spots arranged in second and fourth lines not belonging to the first group Si1 and includes spots SSc at four corners in an outermost circumference of the irradiation pattern. The spots SSc at four corners belong to both the first group and the second group. The aiming beam is sequentially irradiated alternately to the first group Si1 and the second group Si2 at intervals of time ST set so that the aiming spots are not observed simultaneously by the operator's eyes by visual persistence.

Concrete control is explained below. The spots of the group in FIG. 7B and the spots of the group in FIG. 7C are alternately irradiated. The group in FIG. 7B is referred to as first scanning and the group in FIG. 7C is referred to as second scanning. One scanning in each group takes a scanning time (a presenting time) for which the aiming beam spot is turned on and scanned at high speeds so that all the spots in each group are simultaneously recognized by the operator. The switching time ST between the first scanning and the second scanning is set to a time length for which the spots of one group before switching and the spots of the other group after switching are not observed at the same time even by visual persistence of the operator's eye. This time ST is preferably 0.1 seconds or more and 1.0 seconds or less. If the time ST is less than 0.1 seconds, the intermittent interval between the first scanning and the second scanning is short, resulting in difficult observation of the fundus tissues. If the time ST exceeds 1.0 seconds, it is too long to perform aiming of all the spot positions of the 5×5 irradiation pattern. Consequently, the time ST is more preferably 0.2 to 0.5 seconds. In this embodiment, it is set at 0.25 seconds.

In the first scanning, the driving of the scanner 50 and the driving of the aiming light source (or the second shutter 16) are controlled by the controller 70 to irradiate the aiming beam spot at only the spot positions (fifteen spots) in the region Si1 including the four-corner spots SSc. At each spot position, the aiming beam is irradiated with a pulse width Ta (e.g., 3 ms) for a constant time. During spot movement, emission of the aiming beam is stopped. In sync with the emission of the aiming beam, the driving of the galvano mirrors 51 and 55 is stopped so as to introduce the aiming beam to a position corresponding to the spot arrangement. In the case where the driving time of the scanner 50 allowed to operate at high speeds is on the order of microseconds, the spot movement time may be disregarded. Total one scanning time in the first scanning, corresponding to irradiation of fifteen spots of the aiming beam, is about 45 ms. In the case where the time ST is 0.25 seconds (250 ms), scanning is performed about 5.5 times in the first scanning.

After a lapse of 0.25 seconds from the start of the first scanning, the second scanning is performed. In the second scanning, the driving of the scanner 50 and the aiming light source (or the second shutter 16) is controlled by the controller 70 so that the aiming spots are irradiated at only the spot positions (14 spots) in the second group Si1 including the four-corner spots SSc. In this case, one scanning is performed for 43 ms and thus scanning is performed 5.7 times in the second scanning.

The first scanning and the second scanning mentioned above are alternately conducted every 0.25 seconds, thereby allowing the operator to recognize the 5×5 square pattern and check the condition of the tissues in the spot positions in an entire region of the irradiation pattern. At that time, the four-corner spots SSc of the irradiation pattern are irradiated in both in the first scanning and the second scanning. Accordingly, the operator can easily recognize the irradiation range of the 5×5 irradiation pattern and easily determine the target range of the treatment laser beam, adjust a focus, and others. Since the groups are set to include the spots arranged in one line of the irradiation pattern, it is easy for the operator to presume or imagine the positions of the spots not observed simultaneously.

Figure 8A:
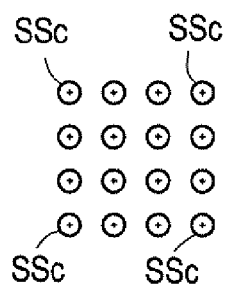
FIGS. 8A-8C are explanatory views showing aiming beam irradiation in a 4×4 irradiation pattern.
Figure 9A:
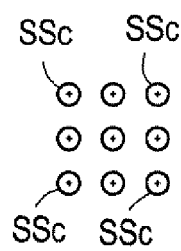
FIGS. 9A-9C are explanatory views showing aiming beam irradiation in a 3×3 irradiation pattern.

As with the above mentioned, even in square patterns of 4×4 and 3×3, spots are divided into two groups each including the spots arranged in a lateral line and the first scanning and the second scanning are switched to irradiate the aiming beam. FIG. 8A is an explanatory view showing the 4×4 square pattern and FIG. 9A is an explanatory view showing the 3×3 square pattern.

Figure 8B:
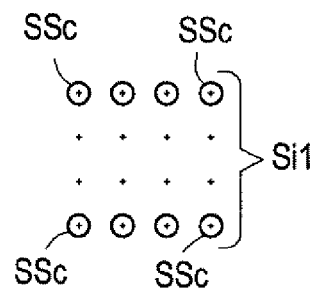
Figure 8C:
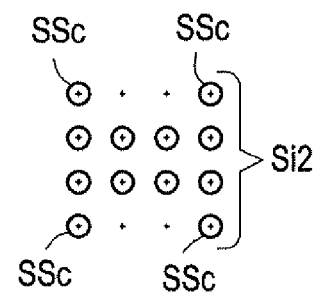

In the 4×4 square pattern, a first group Si1 consists of spots in an uppermost first line and spots in a lowermost fourth line including spots SSc at four corners as shown in FIG. 8B. A second group Si2 consists of spots in second and third lines between the uppermost line and the lowermost line, and the spots SSc at four corners as shown in FIG. 8C. In the case of the 4×4 square pattern, irradiation of the aiming beam is alternately switched at intervals of 0.25 seconds between the first scanning to the first group and the second scanning to the second group.

Figure 9B:
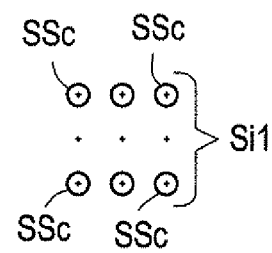
Figure 9C:
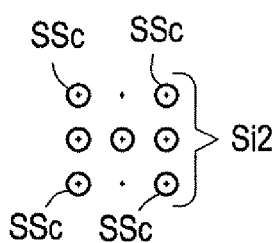

In the 3×3 square pattern, a first group Si1 consists of spots in an uppermost first line and a lowermost third line including spots SSc at four corners as shown in FIG. 9B. A second group Si2 consists of spots in a second line between the uppermost line and the lowermost line and the spots SSc at four corner as shown in FIG. 9C. As with the aforementioned square pattern, irradiation of the aiming beam is controlled to be switched alternately at intervals of 0.25 seconds between the first scanning shown in FIG. 9B and the second scanning shown in FIG. 9C.

Figure 10A:
FIGS. 10A-10C are explanatory views showing aiming beam irradiation in a 2×2 irradiation pattern.
Figure 10B:
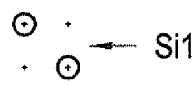
Figure 10C:
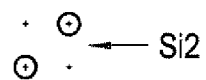

In a 2×2 square pattern shown in FIG. 10A, spots at four corner cover an entire irradiation pattern. In the 2×2 square pattern, a first group Si1 consists of two spots located for example in opposing corners, i.e., upper left and lower right positions, as shown in FIG. 10B. A second group Si2 consists of two spots located in opposing corners, i.e., upper right and lower left positions, as shown in FIG. 10C. The spots in this pattern may also be divided into two spots in an upper line and two spots in a lower line.

Figure 11A:
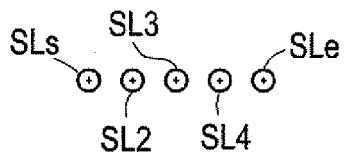
FIGS. 11A-11D are explanatory views showing aiming beam irradiation in a linear pattern.
Figure 11B:
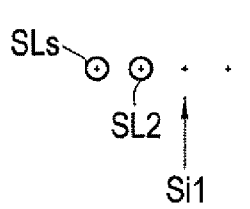
Figure 11C:
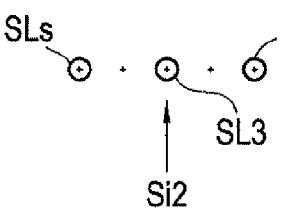
Figure 11D:
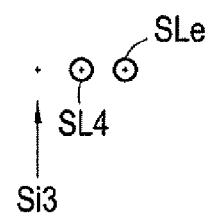

The following explanation is given to irradiation of the aiming beam in a linear pattern. FIG. 11A shows a pattern of five spots SLs, SL2, SL3, SL4, and SLe arranged in a line. In this linear pattern, as with the above square patterns, the spots are divided into a plurality of groups. Preferably, the spots SLs and SLe at both ends of the linear pattern are included in common in each group to facilitate operator's recognition of the range of the linear pattern (an irradiation range). The spots in the pattern consisting of five spots linearly arranged are divided into three groups. A first group Si1 consists of the spots SLs and SLe at both ends and the second spot SL2 from the left as shown in FIG. 11B. A second group Si2 consists of the spots SLs and SLe at both ends and the third spot SL3 from the left as shown in FIG. 11C. A third group Si3 consists of the spots SLs and SLe at both ends and the fourth spot SL4 from the left as shown in FIG. 11D. The driving of the scanner 50 and the irradiation time of the aiming beam are controlled to sequentially irradiate the spots of the aiming beam by switching between the first group Si1, the second group Si2, and the third group Si3 at every interval of time ST. In this example, one spot of the aiming beam is observed as if it is moving in turn to the left in three spot positions between the spots SLs and SLe at both ends. Thus, the operator can perform aiming of each spot and also sequentially observe the tissues located in the three spot positions between the spots SLs and SLe at both ends.

A curve pattern consisting of spots arranged in a curve at equal intervals provides the same manner as the above linear pattern and an explanation thereof is omitted.

A fan-like pattern consisting of spots arranged in three or more lines is explained below. In an example of the fan-like pattern shown in FIG. 12A, spots are arranged in three curved lines. The number of spots is smaller from the upper, outer circumferential side to the lower, inner circumferential side. That is, an uppermost (first) line includes six spots, a middle (second) line includes five spots, and a lowermost (third) line includes four spots. In the case of the fan-like pattern similarly consisting of the spots arranged in three or more lines, the spots are divided into plural groups each group including the spots SSc at four corners. In this example, the spots in the fan-like pattern are divided into three groups. A first group Si1 consists of six spots in the first line and the spots SSc at corners (lower left and lower right positions) as shown in FIG. 12B. A second group Si1 consists of five spots in the second line and the spots SSc at four corners as shown in FIG. 12C. A third group Si3 consists of four spots in the lowermost (third) line and the spots SSc at corners (upper left and upper right positions) as shown in FIG. 12D. The spots of the aiming beam are switched between the groups at every interval of previously set time ST (0.25 seconds). Accordingly, during aiming by irradiation of the aiming beam, it is easy to check the tissues in the positions in which no spot of each group is set. By irradiation of the spots at four corners, an entire irradiation region can be easily ascertained. Since the spots are grouped so that each group include the spots arranged in a line of the irradiation pattern, the spot positions of other groups that are not observed simultaneously are easy to presume.

Figure 12A:
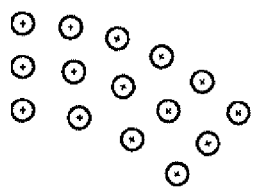
FIGS. 12A-12D are explanatory views showing aiming beam irradiation in a fan-like pattern.
Figure 12B:
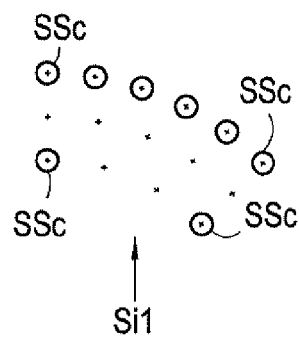
Figure 12C:
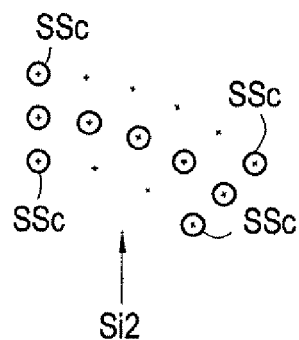
Figure 12D:
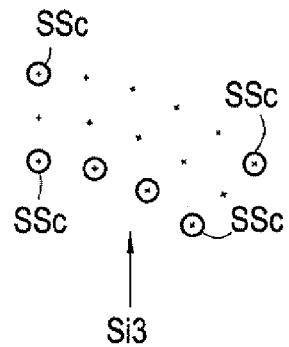

It is to be noted that the spots in the fan-like pattern in FIG. 12A may be divided in the same manner as the square pattern.

Figure 13A:
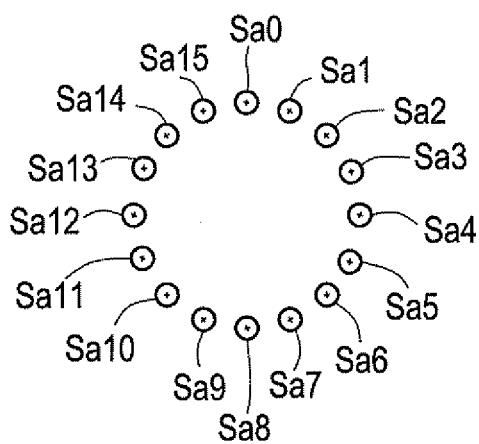
FIGS. 13A-13D are explanatory views showing aiming beam irradiation in a circular pattern.
Figure 13B:
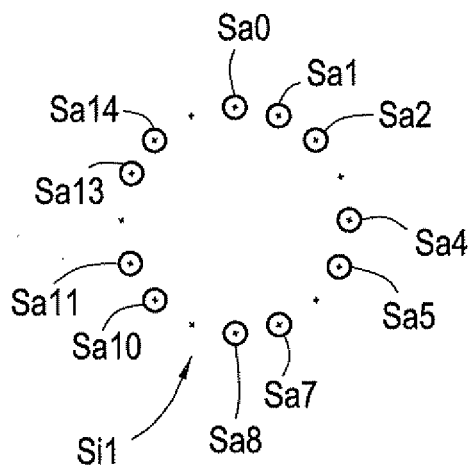
Figure 13C:
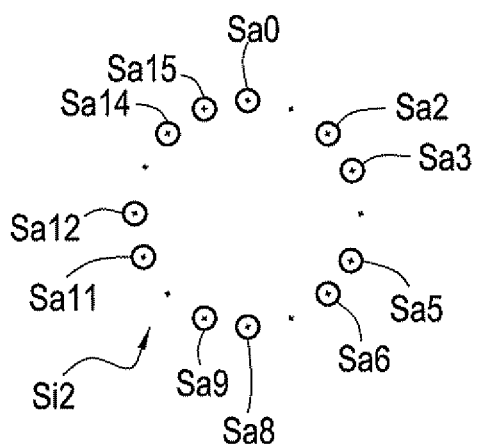
Figure 13D:
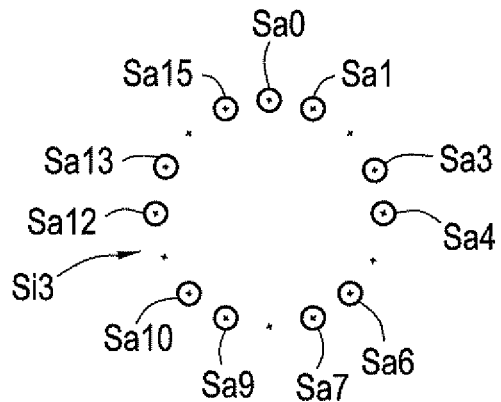

FIG. 13A shows an example of a circular pattern consisting of spots arranged in a single ring form. The circular pattern shown in FIG. 13A includes spots arranged at equal intervals on a circle with a previously determined diameter. Herein, a spot SaO at a start point and sixteen spots Sa1 to Sa15 are arranged. The spots in the circular pattern in FIG. 13A are divided into three groups in each of which adjacent two spots are sequentially arranged by skipping one spot position, the groups being displaced from each other so that vacant or skipped spot positions, each providing a space, are displaced in sequence. It is to be noted that the spot SaO at the start point is included every group in order to allow an operator to clearly ascertain the start point of scanning. A first group Si1 consists of eleven spots SaO, Sa1, Sa2, Sa4, Sa5, Sa7, Sa8, Sa10, Sa11, Sa13, and Sa14, skipping five spots Sa3, Sa6, Sa9, Sa12, and Sa15 and providing spaces therein. A second group Si2 consists of eleven spots SaO, Sa2, Sa3, Sa5, Sa6, Sa8, Sa9, Sa11, Sa12, Sa14, and Sa15, skipping five spots Sa1, Sa4, Sa7, Sa10, and Sa13 and providing spaces therein. A third group Si3 consists of eleven spots SaO, Sa1, Sa3, Sa4, Sa6, Sa7, Sa9, Sa10, Sa12, Sa13, and Sa15, skipping five spots Sa2, Sa5, Sa8, Sa11, and Sa14 and providing spaces therein.

In the circular pattern, similarly, the spots of the first group Si1 to the third group Si3 are scanned by sequential switching at intervals of time ST. Accordingly, the spaces defined by the vacant spot positions are observed by the operator as if the spot positions are moving clockwise. This makes it easy for the operator to observe the tissues in the spot positions other than the spot SaO.

The dividing manner of the circular pattern is not limited to the above example. For instance, a manner of dividing the spots into two groups each consisting alternate spot positions may also be adopted.

Figure 14A:
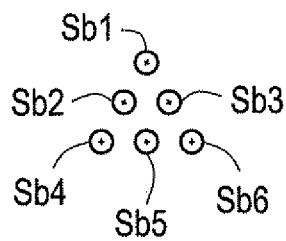
FIGS. 14A-14C are explanatory views showing aiming beam irradiation in a triangular pattern.
Figure 14B:
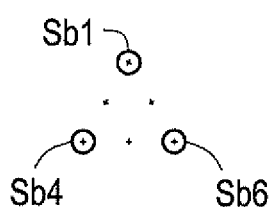
Figure 14C:
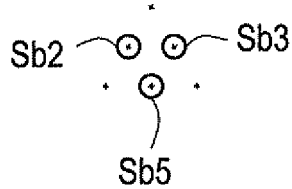

FIG. 14A shows an example of a triangular pattern consisting of six spots arranged in a triangular form. This triangular pattern consists of six spots Sb1 to Sb6 so that three spots are arranged in each side of the triangular form. In this triangular pattern, as shown in FIG. 14B, a first group Si1 consists of spots Sb1, Sb4, and Sb6 at the vertexes of the triangular form, skipping spots Sb2, Sb3, and Sb5 between the vertexes, thus providing spaces therein. To the contrary, a second group Si2 consists of three spots Sb2, Sb3, and Sb5, skipping the spots Sb1, Sb4, and Sb6 at the vertexes, thus providing spaces therein. The first group Si1 and the second group Si2 are switched in turn at intervals of time St, thereby enabling easy observation of the tissues in the spaces and easy aiming of each spot position Sb1 to Sb6.

As above, the spots of the aiming beam to be observed simultaneously by the operator and the spaces of the spots to be unobserved simultaneously are switched in turn. This makes it easy for the operator to observe the fundus tissues in the aiming positions of the aiming beam and also the aiming positions of the aiming beam. Particularly, when the spot size of the aiming beam is set large by use of the zoom lens 42, the fundus tissues become easy to observe. Further, the entire set irradiation pattern can be relatively easily ascertained. It is therefore easy to check the irradiation region of the irradiation pattern, adjust a focus, and others.

In the square patterns (3×3 to 5×5) and the fan-like pattern, the spots at four corners (on the outermost circumference) are continuously visible to the operator. This facilitates recognition of the irradiation region of such a wide pattern as above. As to the linear pattern, the spots at the start point and the end point are continuously visible to the operator, thereby facilitating recognition of the entire irradiation region. As to the circular pattern, the curve pattern, the triangular pattern, and the 2×2 square pattern, each pattern is recognized as if each pattern is entirely rotating, thereby facilitating recognition of the irradiation region.

After completion of the aiming, when the operator presses the footswitch 81, the irradiation of the treatment laser beam is started. Upon receipt of a trigger signal from the footswitch 81, the controller 70 causes the treatment laser source 11 to emit the treatment laser beam and controls the scanner 50 to irradiate the treatment laser beam to each spot position in sequence. The treatment laser beam is irradiated to each spot position for the set time of the pulse width of the treatment laser beam and the spot is moved during a halt time of the treatment laser beam.

In the above explanation, the spots in the irradiation pattern such as the square pattern and the fan-like pattern are divided into groups each including the spots arranged in a lateral line. The present invention is not limited thereto and may be configured so as to include spots arranged in a vertical line.

In the above explanation, the spots in the irradiation pattern such as the square pattern and the fan-like pattern are divided into groups so that every group includes the same spot positions at four corners in each figure. Each irradiation pattern has only to be configured so that each group of the irradiation pattern includes the spot positions at corners. For instance, each group constituting an irradiation pattern in which spots are arranged inside a polygonal or circular form includes the same spots at corners (recognized by an operator).

REFERENCE SIGNS LIST

10 Laser source unit
11 Treatment laser source
12 Aiming laser source
20 Optical fiber
30 Observation optical system
40 Laser irradiation optical system
50 Scanner
60 Illumination optical system
70 Controller
80 Operation unit
100 Ophthalmic laser treatment apparatus

The invention claimed is:

1. An ophthalmic laser treatment apparatus for treating a patient's eye, comprising:
a treatment laser source configured to emit a treatment laser beam;
an aiming light source configured to emit an aiming beam;
an irradiation unit that includes a scanner configured to scan a plurality of irradiation spots formed of at least one of the treatment beam and the aiming beam,
the scanner being arranged to scan the irradiation spots in two dimensions, the scanner scanning each irradiation spot for a first time interval between consecutive spots, and
the irradiation unit being arranged to irradiate the treatment beam and the aiming beam to the patient's eye;
an irradiation pattern setting unit configured to set one irradiation pattern from a plurality of irradiation patterns, each irradiation pattern representing an arrangement of the irradiation spots;
a trigger signal input unit configured to input a trigger signal to start irradiation of the treatment beam; and
a controller configured to:
control the treatment laser source, the aiming light source, and the scanner,
cause the set irradiation pattern to be divided into at least a first group and a second group that each represents a distinct small irradiation pattern, the small irradiation patterns of the first and second groups, when combined together, constitute the irradiation spots of the set irradiation pattern such that irradiation spots of the first group are interlaced with irradiation spots of the second group,
cause sequential irradiation of the aiming beam to tissue of the patient's eye so that an operator is able to observe the irradiation spots of the first group,
cause the sequential irradiation of the aiming beam to the tissue so that the operator is able to observe the irradiation spots of the second group,
cause the sequential irradiation of the aiming beam to the tissue so that (i) the first and second groups are alternatively and repeatedly irradiated, the scanner scanning each group for a second time interval between consecutive groups, the second time interval different from the first time interval, (ii) the operator is able to observe the tissue to be irradiated by the second group when the first group is irradiated, and (iii) the operator is able to observe the tissue to be irradiated by the first group when the second group is irradiated, and
cause sequential irradiation of the treatment laser beam to the tissue, to produce a corresponding set irradiation pattern, based on the trigger signal,
spatial frequencies of the irradiation spots of the first group that are unique to the first group are greater than a spatial frequency of the irradiation spots of the second group that are unique to the second group, and
when the irradiation pattern setting unit sets the irradiation pattern so that the irradiation spots are arranged in a 3×3 square matrix, the controller causes the sequential irradiation of the aiming beam to the tissue so that (i) four corners of the set irradiation pattern in both the first and second groups are irradiated, (ii) regions of the irradiation pattern other than the four corners are alternately irradiated in the first and second groups, and (iii)

the operator is able to observe the treatment area in the regions of the irradiation pattern other than the four corners while continuously observing the irradiation at the four corners.

2. The ophthalmic laser treatment apparatus according to claim 1, wherein
when the irradiation pattern setting unit sets the irradiation pattern so that the irradiation spots are arranged in three or more lines, the controller causes the irradiation spots in the set irradiation pattern to be divided into the first and second groups so that the irradiation spots of the first group are not arranged in the same lines as the irradiation spots of the second group.

3. The ophthalmic laser treatment apparatus according to claim 2, wherein the small irradiation patterns of the first and second groups include irradiation spots at four corners of the set irradiation pattern.

4. The ophthalmic laser treatment apparatus according to claim 1, wherein
when the irradiation pattern setting unit sets the irradiation pattern so that the irradiation spots are arranged in a 5×5 square matrix, the controller causes the irradiation spots in the set irradiation pattern to be divided so that (i) the first group consists of irradiation spots arranged in first, third, and fifth lateral lines and (ii) the second group consists of irradiation spots arranged in second and fourth lateral lines and irradiation spots at four corners of the set irradiation pattern;
when the irradiation pattern setting unit sets the irradiation pattern so that the irradiation spots are arranged in a 4×4 square matrix, the controller causes the irradiation spots in the set irradiation pattern to be divided so that (i) the first group consists of irradiation spots arranged in first and fourth lateral lines and (ii) the second group consists of irradiation spots at the four corners; and
when the irradiation pattern setting unit sets the irradiation pattern so that the irradiation spots are arranged in a 3×3 square matrix, the controller causes the irradiation spots in the set irradiation pattern to be divided so that (i) the first group consists of irradiation spots arranged in first and third lateral lines and (ii) the second group consists of irradiation spots arranged in a second lateral line and irradiation spots at the four corners.

5. The ophthalmic laser treatment apparatus according to claim 1, wherein
when the irradiation pattern setting unit sets the irradiation pattern so that the irradiation spots are arranged in a 2×2 square matrix, the controller causes the irradiation spots in the set irradiation pattern to be divided so that (i) the first group consists of two spots and (ii) the second group consists of two spots that are different from those of the first group.

6. The ophthalmic laser treatment apparatus according to claim 1, wherein
when the irradiation pattern setting unit sets the irradiation pattern so that the irradiation spots are arranged in a linear form, the controller causes the irradiation spots in the set irradiation pattern to be divided so that both the first and second groups include (i) irradiation spots at both ends of the set irradiation pattern and (ii) different irradiation spots between the both ends.

7. The ophthalmic laser treatment apparatus according to claim 1, wherein the second time interval is set in a range of 0.1 to 3.0 seconds.

8. The ophthalmic laser treatment apparatus according to claim 7, wherein the second time interval is set in a range of 0.1 to 0.3 seconds.

9. The ophthalmic laser treatment apparatus according to claim 1, wherein the controller is configured to control emission of the aiming beam from the aiming light source based on the set irradiation pattern.

10. The ophthalmic laser treatment apparatus according to claim 1, wherein
the irradiation unit includes a shutter for blocking the irradiation of the aiming beam to the patient's eye, and
the controller is configured to control opening and closing of the shutter, based on the set irradiation pattern, to control the irradiation of the aiming beam.

11. The ophthalmic laser treatment apparatus according to claim 1, further comprising:
a selector configured to select a mode to irradiate the aiming beam so that the operator is able to simultaneously observe the irradiation spots constituting the set irradiation pattern;
wherein, when the mode is selected, the controller controls a driving speed of the scanner so that (i) the irradiation spots constituting the set irradiation pattern are simultaneously observed by the operator and (ii) the aiming beam is repeatedly irradiated onto the tissue until the trigger signal is input.

12. The ophthalmic laser treatment apparatus according to claim 1, wherein a complete irradiation pattern is formed by the first and second groups.

13. The ophthalmic laser treatment apparatus according to claim 1, wherein the first and second groups are each within a common aiming spot of the aiming beam.

14. The ophthalmic laser treatment apparatus according to claim 1, wherein the second time interval is longer than the first time interval.

15. The ophthalmic laser treatment apparatus according to claim 1, wherein the first time interval is in the range of 3 ms or less.

* * * * *